United States Patent
Rochat

[11] Patent Number: 5,387,174
[45] Date of Patent: Feb. 7, 1995

[54] CENTRIFUGAL SEPARATOR WITH DISPOSABLE BOWL ASSEMBLY

[75] Inventor: Jean-Denis Rochat, Mies, Switzerland

[73] Assignee: Elp Rochat, Mies, Switzerland

[21] Appl. No.: 170,808

[22] Filed: Dec. 21, 1993

[30] Foreign Application Priority Data

Jan. 29, 1993 [CH] Switzerland ............. 276/93

[51] Int. Cl.⁶ ............. B04B 7/02; B04B 7/08
[52] U.S. Cl. ............. 494/10; 494/41; 494/60; 494/80; 494/81; 494/82; 494/84
[58] Field of Search ......... 494/10, 13, 14, 41, 494/43, 44, 56, 60, 65, 80, 81, 82, 84; 210/380.1, 781, 782

[56] References Cited

U.S. PATENT DOCUMENTS

| | | | |
|---|---|---|---|
| 3,145,713 | 8/1964 | Latham, Jr. | 494/41 X |
| 3,409,213 | 11/1965 | Latham, Jr. | 494/41 |
| 4,140,268 | 2/1979 | Lacour | 494/41 |
| 4,300,717 | 11/1981 | Latham, Jr. | |
| 4,767,396 | 8/1988 | Powers | 494/60 |
| 4,795,419 | 1/1989 | Yawn et al. | |
| 4,889,524 | 12/1989 | Fell et al. | |
| 4,943,273 | 7/1990 | Pages | 494/64 X |
| 4,983,158 | 1/1991 | Headley | 494/41 |

FOREIGN PATENT DOCUMENTS

| | | | |
|---|---|---|---|
| 297216 | 1/1989 | European Pat. Off. | 494/43 |
| 64-4820 | 1/1989 | Japan | 494/74 |

*Primary Examiner*—David A. Scherbel
*Assistant Examiner*—Charles Cooley
*Attorney, Agent, or Firm*—Young & Thompson

[57] ABSTRACT

The centrifugal separator for fluids comprises a housing (1a, 1b) in which is mounted a rotatable driving cup (3) of a conical shape widening upwardly, as well as a disposable centrifugal bowl (5) made of an elastomeric material and having a generally conical shape widening upwardly and press fitted in the operative position inside the driving cup. This centrifugal bowl (5) has two annular beads, respectively an upper bead (14) and a lower bead (6), through which extend vertical passages, and it is closed at its upper peripheral end by a metallic bowl cover (11). It further has a cover (16) cooperating with the housing for closing the same above the bowl, a resilient rotatable seal (17) integral with this separator cover and in contact with the bowl cover, and a fluid supply tube (21) extending through the removable cover and integral therewith.

14 Claims, 3 Drawing Sheets

CENTRIFUGAL SEPARATOR WITH DISPOSABLE BOWL ASSEMBLY

FIELD OF THE INVENTION

The present invention is concerned with a centrifugal separator for separating the constituent components of blood (aphaeresis) or other biological fluids, which is to be integrated, for example, into equipment used for the recovery and the sterile filtration of blood before and after an operation, in view of a possible autotransfusion.

BACKGROUND OF THE INVENTION

In the type of apparatus mentioned, the blood recovered is sucked from the operative field, mixed with an anticoagulant solution and then temporarily stored in a filtering container. This blood is subsequently pumped into the bowl of a centrifuge where the red blood cells separate and accumulate under the effect of the high rotational speed attained (approximately 6,000 rpm). When the bowl is full, the red blood cells are washed with a sterile solution and the other components are collected into a recovery bag. At the end of the washing operation, the red blood cells are transferred into a reinfusion bag for a possible later use on the patient.

Centrifugal separators for use in such equipment are already known, for instance those described in the U.S. Pat. Nos. 4,300,717, 4,795,419 and 4,889,524, which include a central body mounted in a rotatable bowl. These separators suffer however several drawbacks, in particular in the manner in which the bowl is mounted in the separator and driven in rotation, both being relatively complicated and expensive. Accordingly, one objective of the present invention is to provide a centrifugal separator of a simpler and less expensive construction than those already known, while making it possible to achieve similar effectiveness. A further objective is to improve the conditions of recovery of the components after separation.

SUMMARY OF THE INVENTION

The centrifugal separator according to the invention is designed for meeting the above objectives and has the following characteristic features:

The centrifugal separator for fluids comprises a housing in which is mounted a rotatable driving cup of a conical shape widening upwardly, as well as a disposable centrifugal bowl made of an elastomeric material and having a generally conical shape widening upwardly and press fitted in the operative position inside the driving cup. This centrifugal bowl has two annular beads, respectively an upper bead and a lower bead, through which extend vertical passages, and it is closed at its upper peripheral end by a metallic bowl cover. It further has a cover cooperative with the housing for closing the same above the bowl, a resilient rotatable seal integral with this separator cover and in contact with the bowl cover, and a fluid supply tube extending through the removable cover and integral therewith.

BRIEF DESCRIPTION OF THE DRAWINGS

The annexed drawing illustrates schematically and by way of example an embodiment of the centrifugal separator according to the invention.

DETAILED DESCRIPTION OF THE INVENTION

Figure 1:
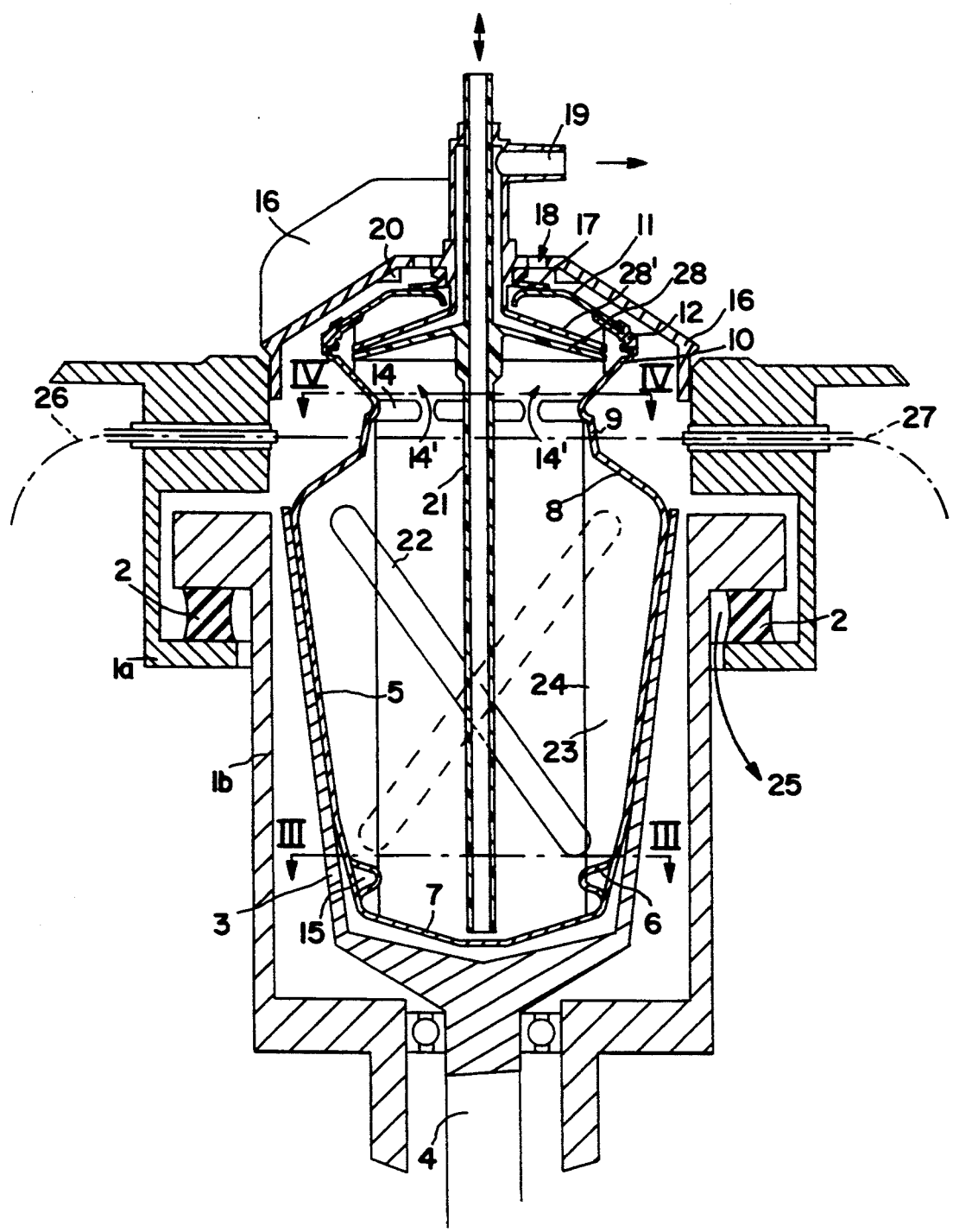
FIG. 1 is a general vertical cross-sectional view.

The centrifugal separator according to the invention, as illustrated by way of example in FIG. 1, comprises a housing formed of two parts 1a and 1b, connected together via an elastic means 2 acting to prevent vibrations from propagating between these two parts. Inside this housing, there is mounted a conical driving cup 3 which extends downwards as a driving shaft 4, in turn driven in rotation by a motor (not illustrated). The housing 1a and 1b, and the driving cup 3 are preferably made from a metal such as aluminum and they form the permanent nondisposable part of the centrifugal separator, which is to be integrated, for example, into a blood processing equipment.

The operative component of the centrifugal separator according to the invention is a centrifugal bowl 5 made of an elastomeric material, preferably produced by extrusion blow-moulding of a synthetic resin. This bowl 5 is of a generally conical shape, with a diameter increasing upwardly; in its lower part, the bowl has an narrowed section forming an annular bead 6 inside the bowl close to the bottom 7 which is also slightly conical. As to the upper part of the bowl 5, it has first a section 8 of oppositely oriented taper extending upwardly into a slightly tapered neck 9, and finally into an open end portion 10 widening upwardly.

Figure 2:
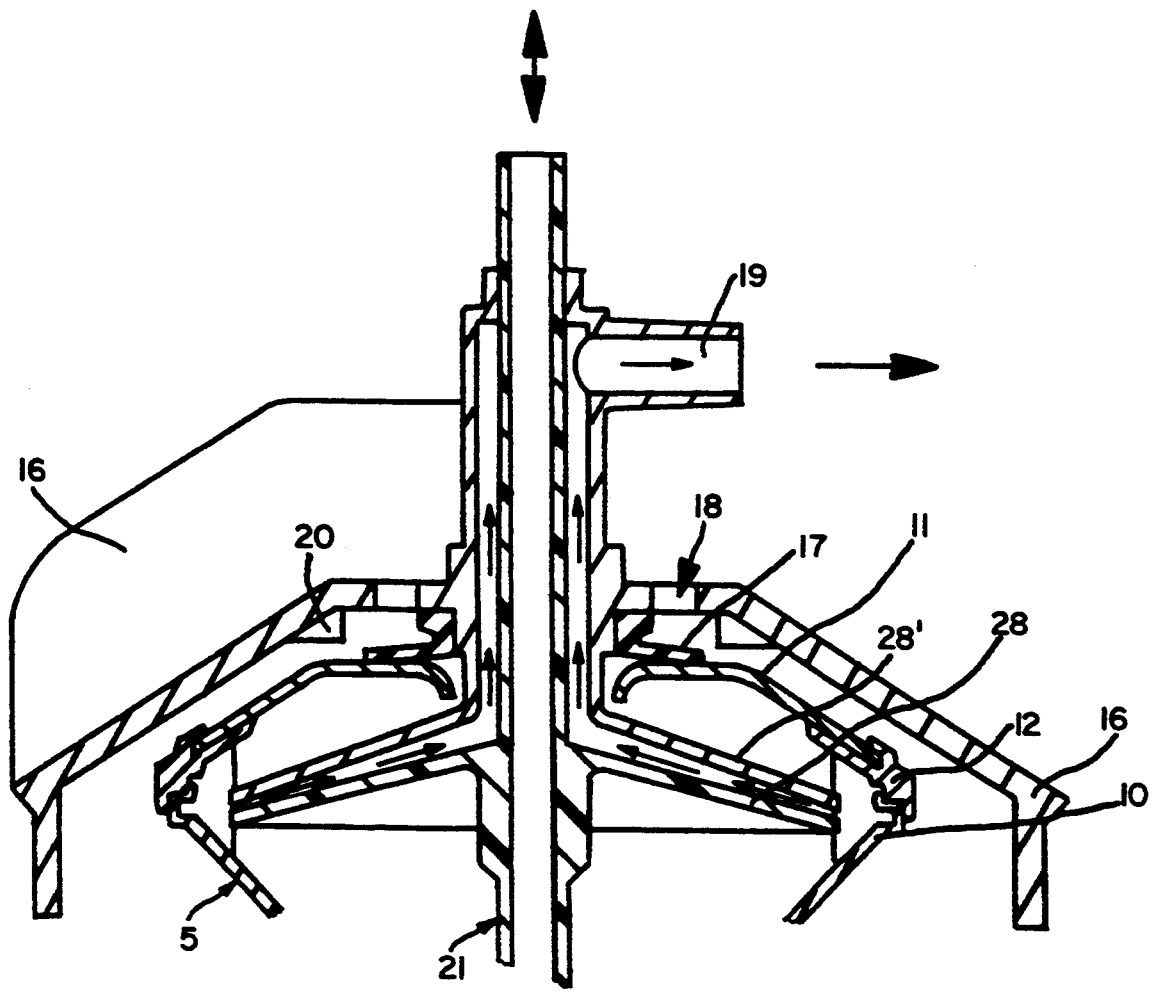
FIG. 2 is a vertical cross-sectional view of a portion of the upper part of the separator, at an enlarged scale.

In the operative position illustrated in FIG. 1, the centrifugal bowl 5 is provided at its upper end 10 with a cover 11, for example made of stainless steel, with an intermediate ring fastener 12 for fastening the cover 11 to said bowl 5 and providing a seal between these two components (FIG. 2). The fastening of the intermediate part 12 to said end 10 of the bowl 5 may be achieved for example by ultrasonic welding.

Figure 3:
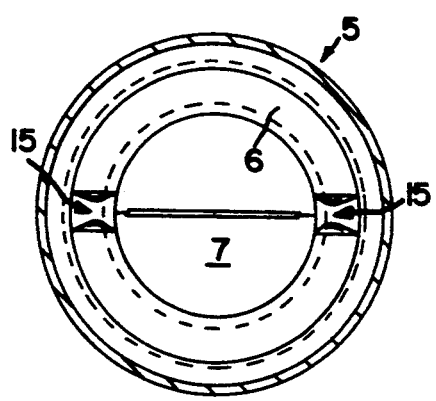
FIGS. 3 and 4 are horizontal cross-sectional views of the rotatable bowl, taken respectively along lines III—III and IV—IV of FIG. 1.
Figure 4:
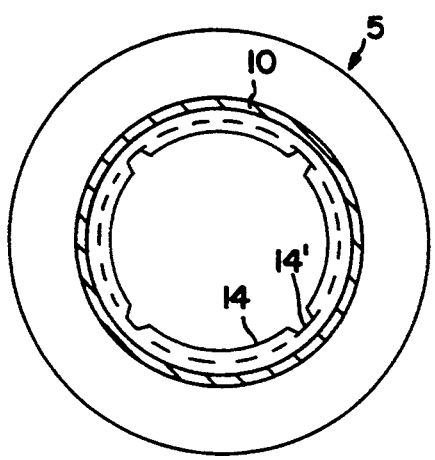

The centrifugal bowl 5 further exhibits an integrally-formed upper annular bead 14, through which extend the vertical passages 14' used as "overflows" (for example 4 such passages are provided) spaced regularly along the periphery of said bead (see FIG. 4). Also, the lower internal bead 6 exhibits two vertical diametrally opposed passages 15, as shown in FIG. 3.

The centrifugal separator according to the invention is closed at its upper end by a cover 16 which is fastened removably by a conventional bayonet type locking system to the upper part 1a of the housing and which is provided on its internal face with a resilient rotatable seal 17, made for example from an elastomer and cooperating in the operative position with the upper surface of the bowl cover 11 for ensuring tightness during the rotation thereof inside the static housing. This cover 16 of the separator is further provided with openings 18 for allowing a ventilation of the contact area between the rotating seal 17 and the bowl cover 11 and also of the bowl 5. Incidentally, the bowl cover 11 and the bowl 5 form the disposable part of the device.

This disposable part also includes a supply tube 21 extending vertically through the cover 16 and integral therewith, its lower open end being located in the operative position close to the bottom 6 of the centrifugal bowl 5, as well as two conical circular components 28, 28' forming two suction lips and a discharge conduit 19 in communication with the space between said suction lips. Finally, mixing blades 22 are provided inside the bowl 5, which are preferably made integral with the wall of the bowl 5 by blow moulding.

The placing of the bowl 5 inside the separator and the locking of the cover 16 can be carried out with one hand. The bayonet type locking mechanism makes it possible to lower the [cover 16—bowl 5—cup 3] assembly by pressing via a stop 20 against the resiliency of the suspension 2, and then allow the assembly to move upwards and be locked in the position illustrated in FIG. 1. At this moment, the stop 20 is out of contact with the cover 11 of the bowl 5, while the cover 11 remains engaged with the rotatable resilient seal 17.

One of the main features of the present invention is the particular geometry of the centrifugal bowl 5. Firstly, the generally conical shape of the bowl (a taper of about 2 to 10 degrees) makes possible a perfect centering thereof inside the cup 3 and ensures it is effectively driven by the cup. The bowl 5 is pressed inside the conical cup 3 with a force of about 20 Newton. The bottom 7 of the bowl 5 is not in contact with the bottom of the cup 3, to ensure the vertical tolerance needed for the proper functioning of the resilient rotatable seal 17.

In known centrifugal separators, the rotatable bowl is associated with a core which is designed for increasing the rate of introduction of the fluid, while preventing the turbulence created by this introduction. Owing to the special geometry of the separator according to the invention, and in particular to that of the centrifugal bowl thereof, it is now possible to delete this core altogether, because the annular bead 6 close to the bottom 7 of the bowl 5 acts as a barrier stabilizing the flow of fluid to be treated entering from the lower end of tube 21, and decreases the perturbations over the entire separation surface. As to the two vertical passages provided 15 in this lower bead 6, their purpose is to create an area of turbulence useful in the washing step. An additional feature of the geometry of the bowl 5 is the presence of the vertical passages 14' extending through the upper bead 14 and spaced regularly at the periphery thereof, which act to spread the outflowing fluid evenly around the bowl periphery and avoid any eccentricity related complications. Finally, the two disks 28, 28', which are integral with the supply tube 21 and the separator cover 16 have preferably a slightly different taper so that the distance of the two lips decreases in the direction of their periphery, which makes it possible to reduce the high tangential speed of the fluid to be sucked up (due to the centrifugal force) and thus ensures a turbulence free evacuation towards the center and then into the discharge conduit 19.

Concerning the operation of the centrifugal separator according to the invention, it is carried out in two phases, as follows:

a) Filling:the mixture to be treated (for example blood) is introduced via the tube 21 at the bottom 7 of the centrifugal bowl 5, so that this fluid first meets the lower bead 6 and flows only through the two supply channels 15, and this without disturbing the separation layer, i.e. the flow remains as close to laminar as possible. The bowl 5 being driven in rotation at a speed of about 10,000 rpm, the red blood cells 23 are trapped against the wall of said bowl and the supernatant 24 (plasma) exits from the top of the bowl 5 through the regulating outflow passages 14' and is discharged from the system four recovery through the discharge conduit 19 (via the suction lips 28, 28').

The control of the level of the fluid inside the bowl 5 is achieved for example by means of a light beam travelling through the upper portion 9 of said bowl (immediately beneath the upper bead 14), between an emitter 26 and a receiver 27 provided in the upper part 1a of the separator and slightly offset with respect to the supply tube 21, to avoid interference therefrom. The passage of the first red cells produces an interruption of the light beam and hence indicates when the bowl 5 is full of red cells. The rotational speed of the bowl is then reduced to about one half until a second detection of red blood cells indicated by the interruption of the light beam stops the supply of blood. At this stage, the hematocrit reading in the bowl 5 is about 80%. The thickness of the plasma being low (see FIG. 2), the process does not cause hemolysis.

b) Washing: the washing consists in mixing physiological saline, introduced trough tube 21, with the red blood cells and in discharging the supernatant loaded with contaminants and various debris. Contrary to the previous phase, the washing, to be effective, is not to be carried out under conditions of laminar flow; advantage is taken of the small area of controlled turbulence where the two supply channels 15 open into the bowl and where the two fluids mix together and to which the red blood cells are brought back at regular intervals of time by the combined effect of short braking operations applied to the centrifuge and the presence of the two mixing blades 22. These short braking operations obviously unsettle momentarily the layered red cells and therefore the washing pump must be stopped a short time before, to avoid loosing too much of the red cells.

Figure 5:
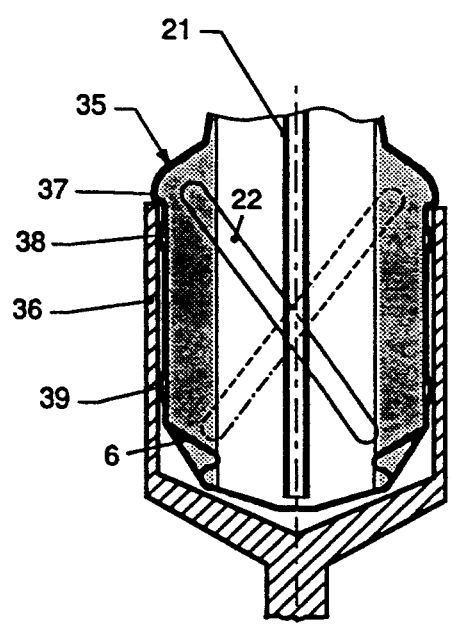
FIG. 5 is a partial vertical cross-sectional view of a variant of the separator shown in FIG. 1, in which the bowl and its driving cup are cylindrical.

In the variant of the separator according to the invention as illustrated partly in FIG. 5, the main wall of the bowl 35 has a cylindrical shape, and so has the driving cup 36. This bowl 35 has also an upper peripheral shoulder 37, which is situated immediately beneath the reversed conical part 8 of the bowl, and which is designed for holding vertically the bowl 35 in the cup 36, so that the bowl does not touch the bottom of the cup. Further, centering studs 38, 39 are provided along the periphery of respectively upper and lower sections of the cylindrical wall of bowl 35 (an average of four studs spaced regularly along the periphery).

Figure 6:
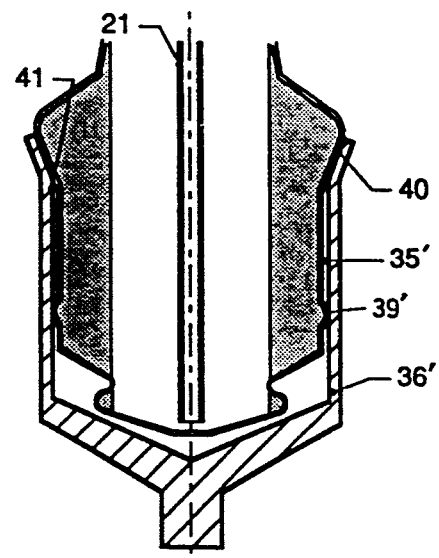
FIG. 6 is a partial vertical cross-sectional view of a modified version of the separator of FIG. 5.

Further, in the version illustrated in FIG. 6, there is also provided a bowl of which the main wall 35' is of a generally cylindrical shape, as well as a matching driving cup 36' and resilient lower centering studs 39'. As to the upper part of the bowl of FIG. 6, it differs from that of FIG. 5 by a conical guiding portion 40 widening upwardly and acting both as a stop means and as a means for holding the bowl inside the cup, in cooperation with a matching upper portion 41 of said cup.

Figure 7:
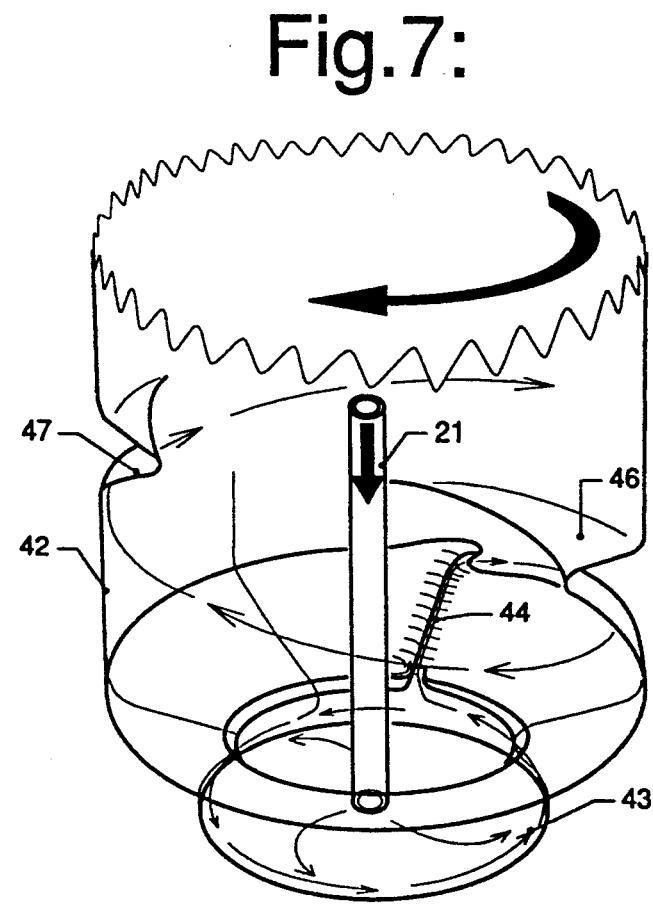
FIGS. 7 and 8 are respectively a partial perspective view and a bottom view of the lower part of the centrifugal bowl of yet another modified version.
Figure 8:
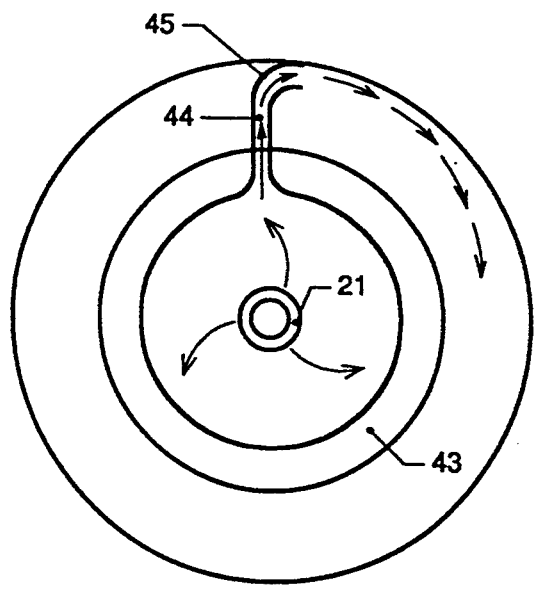

Further, and in order to improve the washing operation, i.e. ensure an efficient mixing of the physiological saline with the red blood cells without loss of the latter, the lower part of the centrifugal bowl was modified as illustrated in FIGS. 7 and 8. In this version, the operation described in relation with FIG. 1 of applying the brake to the centrifuge is avoided. The lower part 42 of the bowl has an annular channel 43 formed by moulding a bead, which is designed for stabilizing the pulsations of the supply pump. Further, this lower part 42 includes one radial channel 44 connecting the annular channel 43 to the cylindrical part of the bowl, which is designed for discharging at increased speed the washing liquid fed into the annular channel 43 from the tube 21 as a compact jet entering the layer of red blood cells deep enough to reach the peripheral wall of the bowl; the flow being turbulent, the washing liquid can mix thoroughly with the red blood cells.

The radial channel 44 has further a curved portion 45 at its outer periphery (in the direction of rotation of the bowl), so as to transform the radial jet into a tangential jet causing the mixture to flow in an ascending spiral.

Finally, a horizontal blade 46 is disposed above the radial channel 44 which makes it possible to limit the vertical speed and avoid too rapid a discharge which would result in a loss of red blood cells. A second blade 47 similar to the first one can be provided above the first one, but in a position diametrally opposite, and having the same purpose. These two blades 46, 47 are preferably also integral with the body of the bowl.

In addition to the obvious simplification of the device due in particular to the total absence of the core inside the centrifugal bowl and hence the lower manufacturing cost, the centrifugal separator according to the invention offers the following advantages over known devices, for example those described in the patents cited in the introductory part:

The geometry of the centrifugal bowl makes it possible on the one hand to separate the constituent components of blood, for example with a high through flow, owing to the laminar nature of the flow of the fluid supplied, and on the other hand to carry out the rinsing of red blood cells in an effective manner under conditions of turbulent flow. Further, although this bowl is designed rather for relatively small volumes of red blood cells (approximately 100 to 150 ml), the high through flow at which the fluid can be treated makes it possible to use this highly effective device practically in any circumstances, even when the volumes to be treated are important.

The small depth of the layer of fluid due to its small volume further offers the further advantage of limiting the pressure, brought about by the centrifugal force, to which the red blood cells are subjected:accordingly, the rotational speed of the bowl can be increased to about 10,000 rpm. whereas in known devices this speed is generally in the order of 6,000 rpm.

The rotational speed given above can also be reached owing to an improved ventilation of the rotatable joint and of the bowl cover: actually, the rotation of the [bowl cover—bowl—cup] assembly produces an intake of air from above (through the orifices 18), which air is expelled at the bottom (through the orifices 25) of the separator, thus creating a draught which cools said assembly; further, the cover of the bowl is made of stainless steel of a high thermal conductivity which assists in transferring the heat to the outside of the bowl, to be evacuated by the convection resulting from the high peripheral speeds.

The flexible rotatable elastomeric seal is frictionally engaged with the cover of the bowl and ensures the tightness needed, both efficiently and at a much lower cost that the seals used in known devices, which generally consist of two members of graphitized rigid resin, which must be machined very carefully to be perfectly planar.

Lastly, the above described system for the control of the passage of the first red cells using an optical fibre instead of detecting a colour transition between the red cells and the plasma which is used in known devices, makes it possible to obtain high hematocrit readings, in the order of 80% instead of the 40–60% achieved with known devices. This further offers the advantage that the volume needed for the washing can be lowered and hence that the consumption thereof can be reduced.

I claim:

1. A centrifugal separator for fluids, comprising: a housing having mounted therein a rotatable driving cup, and a disposable centrifugal bowl made of an elastomeric material, said centrifugal bowl having an external shape matching that of the cup and being press fitted before operation inside said driving cup, said centrifugal bowl including an upper annular bead and a lower annular bead, each of said beads being provided with vertical passages, said centrifugal bowl being closed at a peripheral upper end by a metallic bowl cover, a centrifugal separator cover cooperating with the housing for closing the centrifugal separator above said centrifugal bowl, a flexible rotatable seal integral with said centrifugal separator cover and being in contact with said bowl cover, a tube positioned vertically inside said centrifugal bowl, extending through the centrifugal separator cover and integral therewith, said tube having an open end located close to the bottom of said centrifugal bowl for supplying fluid to be treated, and said tube carrying two conical circular components defining a space therebetween, said circular components acting as suction lips, and said space being in fluid communication with a discharge conduit.

2. A separator according to claim 1, wherein the driving cup and the centrifugal bowl have a generally conical shape widening upwardly.

3. A separator according to claim 1, wherein the driving cup and the centrifugal bowl are of a generally cylindrical shape, and the centrifugal bowl has on its outer cylindrical wall structural means for ensuring vertical positioning and centering of said centrifugal bowl, said structural means cooperating in an operative position with the internal cylindrical wall of said driving cup.

4. A separator according to claim 1, wherein the housing is formed of two superposed parts connected together by resilient means for damping vibrations.

5. A separator according to claim 1, wherein the centrifugal bowl has a lower part which is slightly conical, a main portion, and an upper part comprising a first and a second adjoining conical portion, said first conical portion narrowing upwardly from the main portion, and said second conical portion widening upwardly into an open end, said upper bead being located between the first conical narrowing portion and the second conical widening portion.

6. A separator according to claim 5, wherein the main portion is conical and widens upwardly.

7. A separator according to claim 5, wherein the main portion is cylindrical.

8. A separator according to claim 5, wherein the bowl cover is fastened at its periphery to the open end of said second conical portion with an intermediate ring fastener.

9. A separator according to claim 5, wherein the lower part of the centrifugal bowl is provided with an annular channel and with a radial channel connecting the upper part of the centrifugal bowl, said radial channel having a peripheral end portion which is curved in the direction of rotation of the centrifugal bowl.

10. A separator according to claim 9, wherein at least one horizontal blade is positioned above the radial channel, and wherein said annular channel, said radial channel, and said at least one horizontal blade are all integral with the centrifugal bowl.

11. A separator according to claim 1, wherein mixing blades integral with the centrifugal bowl are provided inside the centrifugal bowl.

12. A separator according to claim 1, wherein the centrifugal separator cover includes means for fastening it to the housing, and said centrifugal separator cover includes ventilation openings.

13. A separator according to claim 1, further including immediately beneath said upper bead of the bowl, an emitter for emitting a light beam and a receiver for receiving said light beam.

14. A separator according to claim 1, wherein said conical circular components acting as suction lips have different angles of taper, so that the distance between said conical circular components decreases in the direction of their periphery.

* * * * *